United States Patent
Valunin et al.

[11] Patent Number: 6,015,435
[45] Date of Patent: Jan. 18, 2000

[54] SELF-CENTERING PHAKIC INTRAOCULAR LENS

[75] Inventors: Igor Valunin, Cincinnati; George W. Rozakis, North Olmsted, both of Ohio

[73] Assignee: International Vision, Inc., Cincinnati, Ohio

[21] Appl. No.: 08/955,917

[22] Filed: Oct. 22, 1997

Related U.S. Application Data

[60] Provisional application No. 60/029,103, Oct. 24, 1996, and provisional application No. 60/029,341, Oct. 31, 1996.

[51] Int. Cl.[7] ..................................................... A61F 2/16
[52] U.S. Cl. ............................................................. 623/6
[58] Field of Search ................................................ 623/6

[56] References Cited

U.S. PATENT DOCUMENTS

| | | | |
|---|---|---|---|
| 4,277,851 | 7/1981 | Choyce | 3/13 |
| 4,414,694 | 11/1983 | Choyce | 3/13 |
| 4,573,998 | 3/1986 | Mazzocco | 623/6 |
| 4,585,456 | 4/1986 | Blackmore | 623/6 |
| 4,710,197 | 12/1987 | Donn et al. | 623/6 |
| 4,769,035 | 9/1988 | Kelman | 623/6 |
| 4,863,462 | 9/1989 | Fedorov et al. | 623/6 |
| 4,932,970 | 6/1990 | Portney | 623/6 |
| 5,019,099 | 5/1991 | Nordan | 623/6 |
| 5,047,051 | 9/1991 | Cumming | 623/6 |
| 5,074,877 | 12/1991 | Nordan | 623/6 |
| 5,078,742 | 1/1992 | Dahan | 623/6 |
| 5,201,763 | 4/1993 | Brady et al. | 623/6 |
| 5,236,452 | 8/1993 | Nordan | 623/6 |
| 5,258,025 | 11/1993 | Fedorov et al. | 623/6 |
| 5,443,507 | 8/1995 | Jacobi | 623/6 |
| 5,480,428 | 1/1996 | Fedorov et al. | 623/6 |

FOREIGN PATENT DOCUMENTS

| | | |
|---|---|---|
| 2093097 | 10/1993 | Canada. |
| 537643 | 4/1993 | European Pat. Off.. |
| 88/00180 | 4/1993 | WIPO. |

OTHER PUBLICATIONS

Mazzocco, et al., Soft Implant Lenses in Cataract Surgery, Slack, Inc., 1986, p. 93.

Fechner, et al., J. Cataract and Refractive Surgery, 22:178–181 (Mar. 1996).

*Primary Examiner*—Mickey Yu
*Assistant Examiner*—Kelly O'Hara
*Attorney, Agent, or Firm*—Frost & Jacobs LLP

[57] ABSTRACT

A phakic intraocular lens (IOL) for the correction of visual disorders such as myopia, hyperopia, astigmatism and presbyopia. The lens is made from a biocompatible, elastomeric material such as silicone. The lens further includes one or more annular surfaces that protrude from the anterior surface of the lens or surrounds the lens such that when placed in the eye, it makes contact with the iris. As the iris dilates and constricts, the contact with the iris places a centering force on the implanted lens. The lens is not in contact with the natural lens of the eye and floats in the posterior chamber without insult or abrasion to surrounding tissue.

11 Claims, 8 Drawing Sheets

SELF-CENTERING PHAKIC INTRAOCULAR LENS

TECHNICAL FIELD

This application is based on U.S. Provisional Patent Application No. 60/029,103, filed Oct. 24, 1996 now abandoned, and U.S. Provisional Patent Application No. 60/029,341, filed Oct. 31, 1996 now abandoned.

The present invention relates to an intraocular lens for the correction of visual disorders.

BACKGROUND OF THE INVENTION

According to "Intraocular Lenses," authored by Dr. David J. Apple, published by Williams and Wilkins, 1989, evidence of the concept of intraocular lenses dates back at least two centuries. An 18th century oculist named Tadini proposed the idea of a lens implant and even attempted the development of one. The first recorded implant was by Casaamata around 1795, which failed due to inadequate fixation of the implant to the surface of the eye. The first successful series of implants is credited to Dr. Harold Ridley of London. Ridley observed fragments of an acrylic plastic material used in World War II fighter canopies lodged in the eyes of fighter pilots he treated. Finding no biologic reaction, he chose to use this rigid material for his first intraocular lens implants. A clinical quality version of the material, polymethylmethacrylate (PMMA), more commonly known as Plexiglass, was fabricated by Rayners of London into the first synthetic intraocular lenses (IOL).

Inflammation was commonly observed as a major complication when these early lenses were used. Ridley, however, considered moderate postoperative inflammation to be beneficial because it created adhesions to affix the lens implant. Factors which contributed to the development of postoperative inflammation included residues on or in the lenses of the sterilizing compounds, disinfectants, polishing compounds, or additives which were added to control polymerization, as well as rough or sharp edges, holes, or ridges on the intraocular lens itself. Poor lens design suppressed the growth of IOL's until the design improved and the market grew rapidly in the 1980's.

According to "Intraocular Lens Implantation" by Dr. Emanuel S. Rosen, et al., published by The C.V. Mosby Company, 1984, intraocular lens implant procedures are used primarily for the correction of cataracts, a disease that affects the clarity of the natural lens. For the lens of the eye to remain functional it must maintain its shape and transparency. The embryonic lens is formed by layers of epithelial cells that elongate, form a crystalline structure and become optically clear. This formation process slows down but continues throughout life. The process can be upset by a number of environmental insults including old age, chemical contamination or physical injury. Any of these can trigger the formation of crystalline structures that occur within the lens itself. The newly formed crystalline structures scatter light and destroy the transparency of the lens. In cataract treatment, the IOL replaces the natural lens.

Intraocular corrective lenses for the treatment of refractive errors is a logical evolution of the cataract replacement IOL technology. Corrective lenses (eyeglasses, contact lenses) have been the mainstay for the correction of visual acuity defects. Myopia (nearsightedness), hyperopia (farsightedness), astigmatism and presbyopia (loss of near vision due to factors such as natural lens inflexibility) can all be treated with eyeglasses and contact lenses. Phakic lenses are ones which are used in combination with, rather than in place of, the natural lens in the eye. However, the use of phakic IOLs has generally been unsuccessful due to design related issues that cause insult to the natural lens resulting in such complications as cataracts or abrasion of surrounding tissue.

Refractive surgery is an alternative for treatment of certain types of visual acuity defects. Radial keratotomy (RK) and photorefractive radial keratectomy (PRK) are useful in treating mild to moderate myopia of 6 diopters or less and have shown limited success in treating astigmatism. The effectiveness of these procedures is less predictable in patients with higher degrees of myopia and cannot be used to treat hyperopia or presbyopia. Neither procedure is without significant postoperative events. The hyperopic shift and corneal instability following radial keratotomy and the high incidence of postoperative corneal haze, halos and starbursts with PRK are well documented in the literature. Additionally, both procedures produce overcorrection (hyperopia) and undercorrection (residual myopia) in a significant number of patients. Laser intrastromal in situ keratomilieusis (LASIK) is a new refractive surgery procedure that, in an experienced surgeon's hands, can treat both low and high degrees of myopia, hyperopia and astigmatism. Preliminary data indicate that LASIK produces few postoperative visual events, postoperative vision stabilizes rapidly compared to RK and PRK, and LASIK does not appear to produce any residual weakening in endothelial structure.

The phakic IOL fills the gaps in refractive surgery treatment modalities for visual acuity defects of all types, including astigmatism and, potentially, presbyopia, assuming that the shortcomings, discussed above, can be dealt with effectively. Such lenses are indicated for any level of myopia or hyperopia, including correction beyond 6 diopters.

The basic concept of phakic IOLs was disclosed in U.S. Pat. No. 4,585,456, Blackmore, issued Apr. 29, 1986. Blackmore describes a phakic lens which is placed on the surface of the natural lens and centered by being held in the ciliary sulcus. This approach failed to provide safe and effective treatment due to such complications as insult to the natural lens causing cataracts, abrasion of the pigment of the iris causing angle closure glaucoma and pupilary block glaucoma caused by blocking the flow of the eye's aqueous fluid through the pupil. Fixation of the lens using the interaction of the haptics and the ends of the ciliary sulcus requires proper measurement of the eye and selection of the proper haptic size (diagonal dimension across the lens and haptic). Improper haptic size can result in decentration of the implanted lens which leads to improper vision. See also, Mazzocco, et al., Soft Implant Lenses in Cataract Surgery, Slack, Inc., 1986, p. 93, Model E (a phakic lens fitting in the ciliary sulcus). Several other corrective lens implants having stiffened or rigid haptics, such as those described in U.S. Pat. No. 5,258,025, Fedorov, et al., issued Nov. 2, 1993, and U.S. Pat. No. 5,078,742, Dahan, issued Jan. 7, 1992, can result in similar complications. These complications are documented by Fechner, et al., in the Journal of Cataract and Refractive Surgery, March, 1996, vol. 22, pp. 178–81. Fechner also makes the observation that a cataract can form where the intraocular lens is in contact with the natural lens. Sustained contact between the implanted lens and natural lens can insult the natural lens by staving it of oxygen or nutrients provided in the aqueous fluid of the eye resulting in formation of a cataract. See also, U.S. Pat. No. 4,769,035, Kelman, issued Sep. 6, 1988, which discloses a phakic intraocular lens which sits directly on the anterior surface of the natural lens.

PCT/SU88/00180, assigned to Mikrokhirurgiya Glaza, published Apr. 21, 1993, discloses an anterior chamber lens that also has proven to result in significant complications when used. This lens has a means for iris centration that requires the lens to protrude into the anterior chamber; a spool-shaped surface on the lens restricts the movement of the iris. This concept also limits the optical diameter of the lens. The design places all or part of the lens surface in the anterior chamber of the eye and the edges of the spool scatter light creating haloes in the patients vision even during periods of bright ambient light. Also, restricting the movement of the iris results in pigment abrasions and potential trauma to the iris. The maximum diameter or diagonal dimension measured across the optic and haptics is small (less than 10.5 mm) because it is not necessary for the haptics to be centered by the ciliary sulcus or the ciliary zonules since the spool-shaped edges of the optic body are centered in the pupil of the eye by the iris.

A corrective lens that sits on the natural crystalline lens and uses the curvature of the natural lens to center the optic body is disclosed in U.S. Pat. No. 5,480,428, Fedorov et al., issued Jan. 2, 1996. This lens is made from inflexible materials and requires surgical insertion without substantial deformation of the haptic or the optic bodies, thus requiring an incision and suturing to close it. The approach requires a port or hole in the optic body to allow flow of the eye's aqueous fluid. Surgeons have overcome complications related to blocking the pupil by creating a hole in the iris (an iridotomy) to permit the natural flow of the eye's aqueous fluid from the posterior chamber to the anterior chamber of the eye.

It would be highly desirable to develop a phakic intraocular lens which did not have the problems associated with the prior art lenses. The present invention overcomes these problems by:

(1) allowing the lens to float freely in the aqueous solution of the eye's posterior chamber;

(2) providing haptics that can move and flex with the anatomy of the eye;

(3) using a self-centration means that does not abrade or restrict the movement of the iris;

(4) providing haptic bodies in combination with the optic body that capture the natural flow of the aqueous fluid of the eye to create a fluid layer between the implanted lens and the natural lens; and (5) assisting the circulation of the aqueous fluid of the eye between the natural lens and the implant by utilizing the movement of the iris.

SUMMARY OF THE INVENTION

The present invention is a phakic, intraocular corrective lens for the correction of visual disorders such as myopia, hyperopia, astigmatism and presbyopia. The invention comprises an optical body and one or more haptic bodies. The optical body has a lens for the refraction of light at an appropriate optical power to correct a visual disorder. The refractive lens can be negative or positive. The haptic bodies are of such size and shape that they cannot contact the outermost circumference of the ciliary sulcus at the same time (i.e., the lens is not held in place at the ciliary sulcus by the haptic bodies).

The invention is made of a biocompatible, elastomeric material, such as silicone, with a very smooth surface that will not abrade or insult the eye or provide areas where leukocytes and other deposits can collect. The invention may also be made of polymethylmethacrylate, polyhydroxyethylmethacrylate, collagen/acrylic blends and other materials which may be hydrophobic, hydrophilic or gas permeable. The implanted lens floats in the posterior chamber of the eye without touching the natural lens, permitting the implanted lens to move when very small forces are applied to it.

The haptic body(ies) included in the present invention are generally nonplanar with substantially uniform thickness and a shape that approximates the curvature of the natural lens or are substantially spherical. The haptic body(ies) assure that the lens cannot be grossly decentered in the pupil of the eye by making contact with the periphery of the posterior chamber in the area of the ciliary sulcus if such decentration occurs. The haptic(s) is preferably flexible in the direction of the optical axis of the lens so that it will follow the changing radius of the natural lens as the eye accommodates to focus on near or far objects.

The lens of the present invention further includes one or more annular surfaces that protrude from the anterior surface of the lens such that the annular surface is in the path of the iris as it dilates and constricts to adjust the aperture or pupil of the eye for variations in ambient light. Contact by the moving iris places a centering force on the protruding annular surface(s) to move and maintain the lens centered in the pupil of the eye. When the lens is centered, and as the iris continues to constrict, the protruding annular surface(s) is shaped so as not to prevent movement of the iris but rather to allow it to slide over the protruding surface. The protruding surface(s) is contoured, radiused, or beveled to assure that it does not abrade the iris as this sliding takes place. The protruding surface(s) can either be part of the optical body or can be a separate portion of the lens. The surface(s) can be parallel to the optical axis of the eye or ramped to assure that the iris can slide up (in the anterior direction) and over the optical body of the lens.

The annular protruding surface(s) described above must be of such size, shape and location that its entire surface is within the pupil of the eye when dilated at its maximum aperture. The maximum aperture is achieved in the dark, each night as the patient sleeps, or when dilation is achieved by medication. If the lens becomes decentered beyond the maximum aperture of the pupil, the protruding annular surface will act to decenter the lens rather than to center it. Therefore, to assure the protruding annular surface is appropriately centered, the haptic body(s) reaches into the periphery of the posterior chamber of the eye to prevent gross decentration. A similar action occurs with positive lenses where the convex anterior surface of the lens itself protrudes to receive the centering force applied by the iris as it constricts.

The constricting and dilating action of the iris acts on the protruding annular surfaces to move the optic and haptic bodies of the lens to create or assist in the flow and circulation of the eye's surrounding aqueous fluid such that oxygen and nutrients in the said fluid reach the natural lens.

There is great utility and commercial value for corrective lenses that are implantable in the posterior chamber of the eye to correct visual acuity defects, but the complications which accompany the use of such devices have prevented past attempts from being successful. The present invention overcomes these complications by permitting the lens to float freely in the aqueous solution of the eye rather than being held in place by the haptics or other fixation methods such as by contact between the posterior of the lens and the curvature of the natural lens or fixation in the ciliary sulcus. A free floating, implanted lens will maintain a layer of aqueous fluid between it and the natural lens by capturing the natural flow of the aqueous fluid of the eye to bias the implanted lens away from the natural lens (i.e., unlike many prior art lenses, the lens of the present invention does not rest directly on the natural lens). The low frictional force created by allowing the lens to float freely permits lens centering forces to be applied to the lens by the iris via the protruding annular surfaces described. The present invention allows the lens to be self-centered rather than requiring that it be held in place by spring loaded haptics, flexible haptics, stiffened haptics, rigid haptics, by adhering to the natural lens or other structures of the eye, or by other fixation methods. The net result is a phalic intraocular lens which provides optical correction without damaging the delicate structures of the eye.

Other objects and advantages of the invention will become more apparent from the following specification taken in conjunction with the figures herein. These figures are intended to be exemplary and not limiting of the present invention.

BRIEF DESCRIPTION OF THE DRAWINGS

FIG. 1a is a cross-sectional view of a positive corrective lens (11) with an optical body (12) and two haptic bodies (13) having thin and substantially uniform thickness (129), where the optical body comprises a convex anterior surface (14) and a concave posterior surface (15) that is a continuation of the posterior surface of the haptic bodies (16). FIG. 1b shows a similar cross-sectional view of a negative corrective lens (17) with an optical body (18) and two haptic bodies (19) where the optical body comprises a concave anterior surface (120) and a concave posterior surface (121) that is a continuation of the posterior surface of the haptic bodies (122). The negative lens in FIG. 1b has an annular protruding surface (123) where the iris may place a centering force on the lens. Likewise, the positive lens of FIG. 1a has an annular peripheral area (protruding surface) of the lens (122) that is sufficiently steep and protrudes into the path of the iris such that the iris may place a centering force on the lens as it constricts and slides up and over the convex anterior surface (14). Both lenses have an optical axis (128).

FIG. 1c shows a positive lens (124c) and FIG. 1d shows a negative lens (124d) with optical body (125) and haptic bodies (126) having a posterior concave surface (127) such that the radius of curvature of the lens posterior concave surface is less than the radius of curvature of the posterior surface (129) of the two haptic bodies (126). Annular protruding surface (123d) shows another potential embodiment of this invention wherein a ramped surface is provided to assure there is no trauma to the iris as it contacts the surface and slides over it.

FIG. 1e shows the curvature of the natural lens (130) prior to accommodation and FIG. 1f shows the curvature of the natural lens (131) during accommodation where it is steeper than the surface (130) shown in FIG. 1e.

FIG. 3f is the top view of the lens which corresponds to the cross-section in FIG. 2a.

FIG. 3a through 3g show several embodiments of the haptic body which may be used in the present invention. FIG. 3a shows an implantable lens (31) with an optical body (32) and two haptic bodies (33) where the optical body has a tangent point or tangent area (34) with the edge of the lens and/or with the annular protruding surface (123 in FIG. 1a & b). FIG. 3b shows an implantable lens (35) with an optical body (36) and a haptic body (37) where the optical body and annular protruding surface(s) (123 in FIG. 1a or b, or 21 in FIG. 2a) are within the edges of the haptic body (37). FIG.

3c shows a similar embodiment with concave cut outs (38) on the short sides of the haptic (39). FIG. 3d and 3e show other haptic (310) placements and designs. FIG. 3f shows a top view of the stepped lens configuration from FIG. 2a. FIG. 3g shows the annular protruding surfaces as partial segments (311); this represents an embodiment where the width of the lens is reduced by truncating a portion of the optical body to facilitate insertion through a small incision in the eye. As can be seen, the haptic bodies are attached to the optical body and extend outward therefrom in at least two generally opposite directions (i.e., bilaterally). These embodiments are intended to be representative examples of the many haptic designs which may be used in the intraocular lens of the present invention.

DESCRIPTION OF THE PREFERRED EMBODIMENTS

Figure 1:
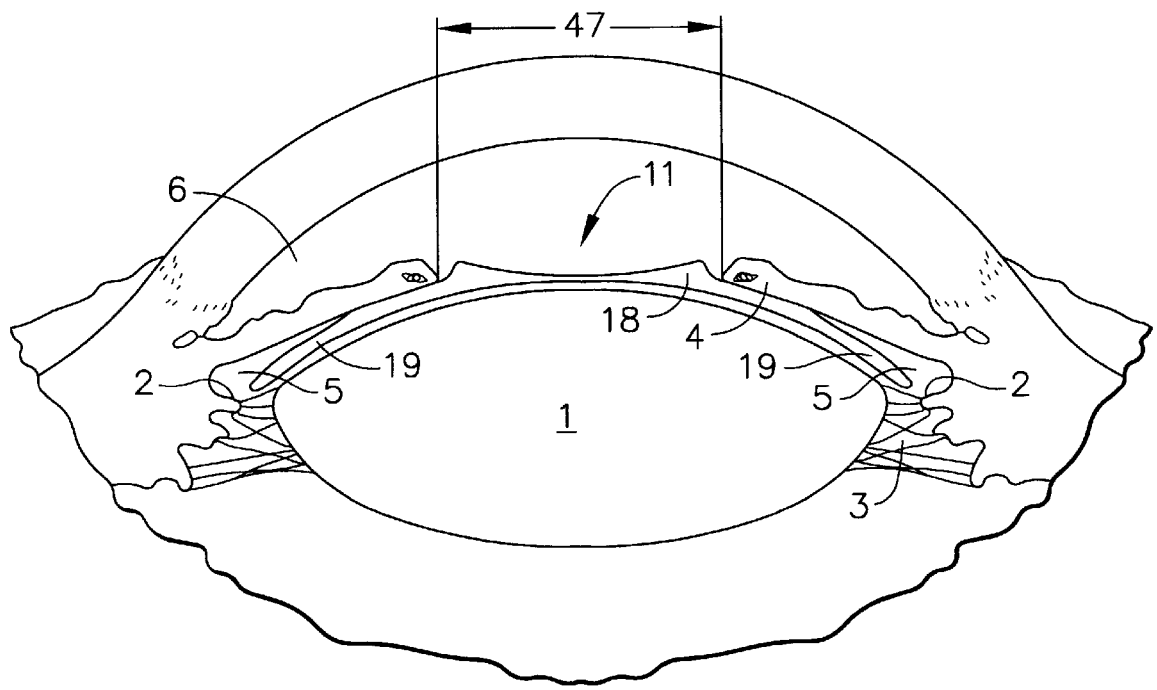
FIG. 1 is a cross-sectional view of the eye showing one embodiment of the lens of the present invention (11) positioned in the posterior chamber of the eye (5). The ciliary sulcus (2) and the zonual fibers (3) are also shown. The optical body (18) and the haptic bodies (19) are not in constant contact with the natural lens (1). Contact with the zonuals (3) or ciliary sulcus (2) can occur dependent upon the size or anatomy of the eye in relation to the implanted lens. The lens is held in contact with the iris (4) by the flow of the aqueous solution of the eye that naturally flows through the zonual fibers (3) into the posterior chamber of the eye (5). Continuity of flow into the anterior chamber of the eye (6) is maintained by an iridotomy (surgical opening in the iris) (4).
Figure 1A:
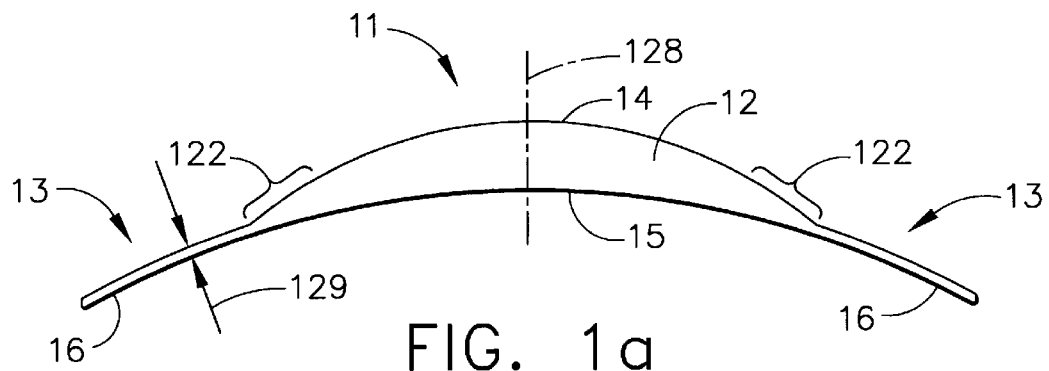
FIGS. 1a and 1b are cross-sectional views of two basic embodiments of the present invention.
Figure 1B:
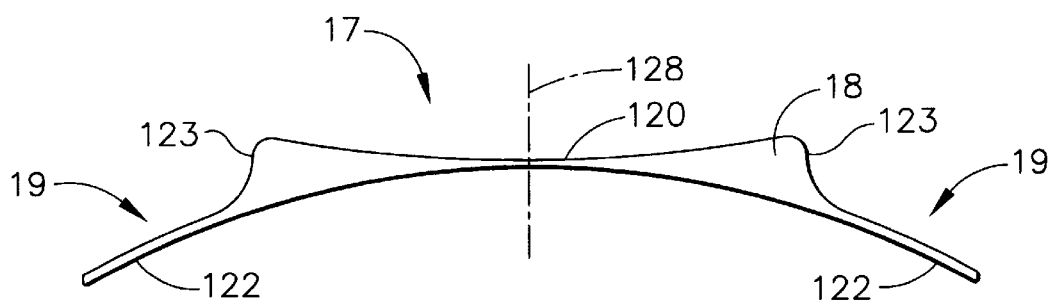
Figure 1C:
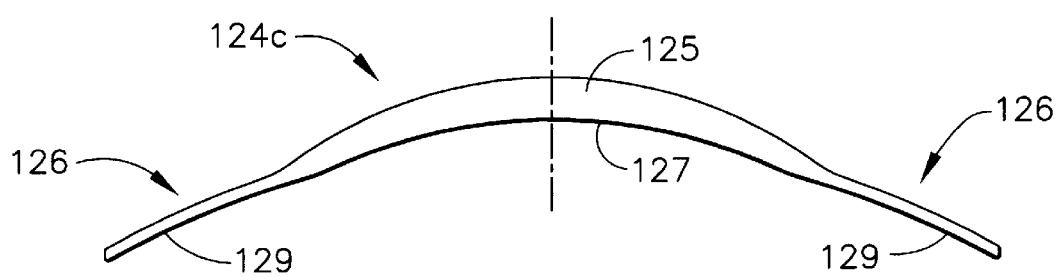
FIGS. 1c and 1d show cross-sectional views of two other embodiments of the present invention.
Figure 1D:
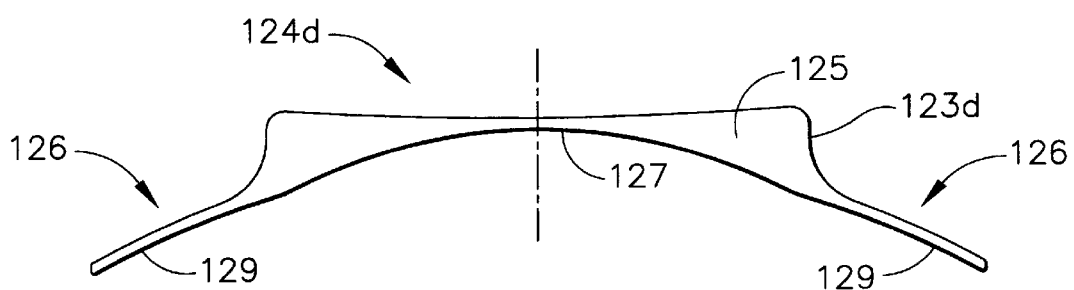
Figure 1E:
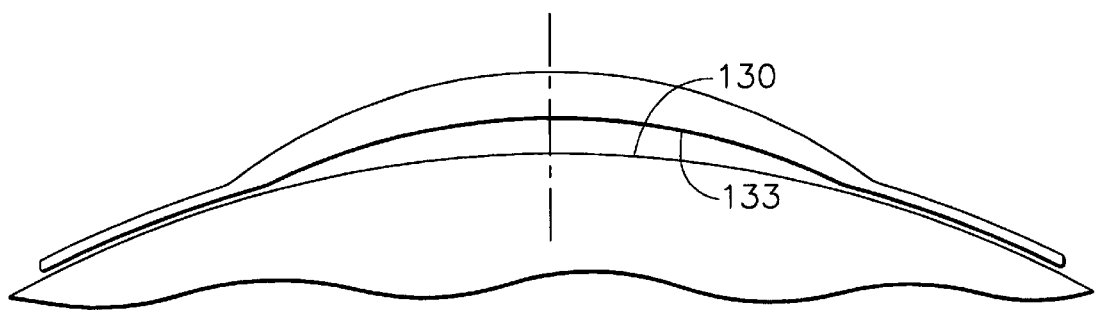
FIGS. 1e and 1f show how the smaller radius of the optical body (127 in FIG. 1c & 1d) (compared to the haptic radius) assures that as the haptic flexes to conform to the changing radius of curvature of the natural lens (131), the probability of contact with the natural lens at its apex (148) is reduced.
Figure 1F:
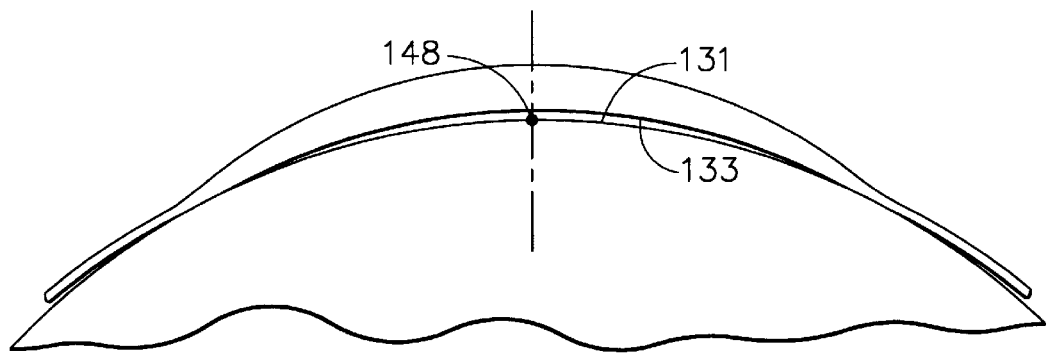
Figure 1G:
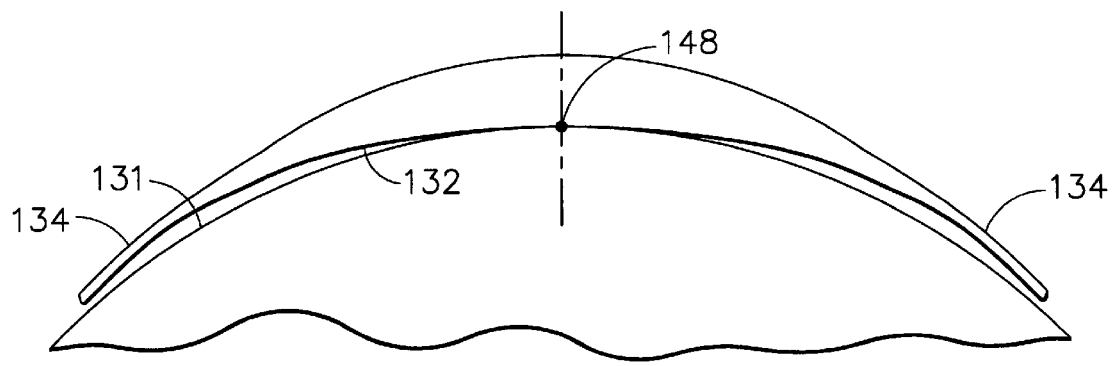
FIG. 1g shows the condition where the radius of the posterior surface (132) is larger than the radius of curvature of the posterior surface of the optical body (133) shown in FIG. 1e. The natural lens (131) has curved during accommodation and the haptic (134) has flexed to follow the changing curvature. This potentially creates a contact point (148) which can cause injury to the natural lens.
Figure 3F:
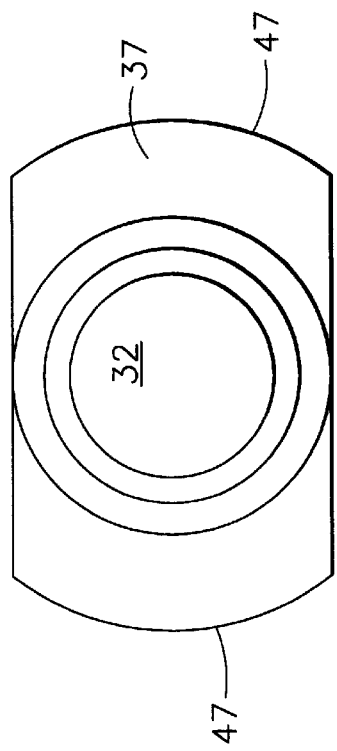
Figure 3G:
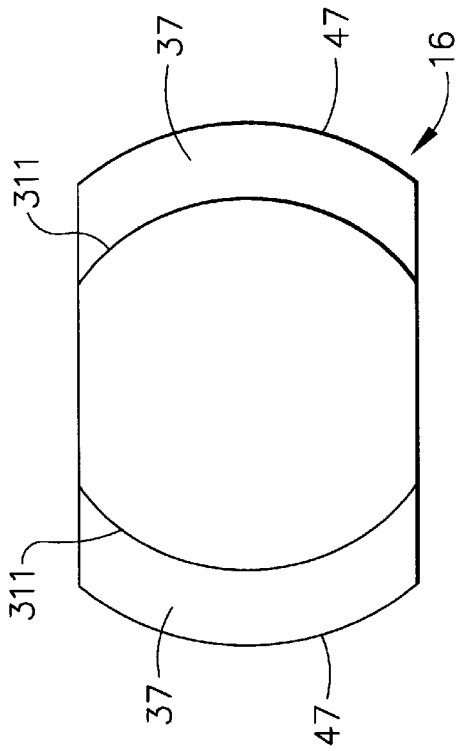
Figure 3A:
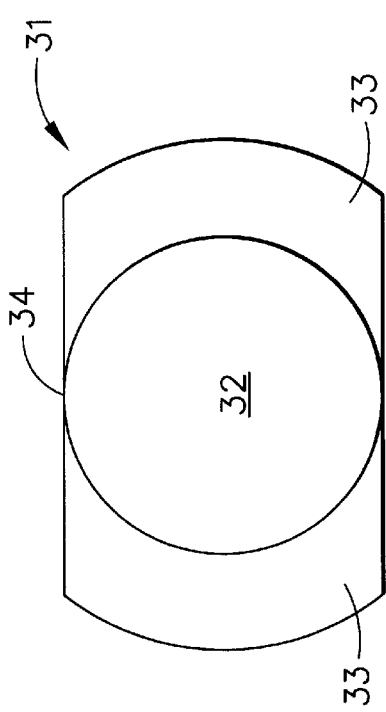
FIG. 3a is the top view of the lens which corresponds to the cross-section in FIG. 1a, and FIG. 3b is the top view of the lens which corresponds to the cross-section in FIG. 1b.
Figure 3B:
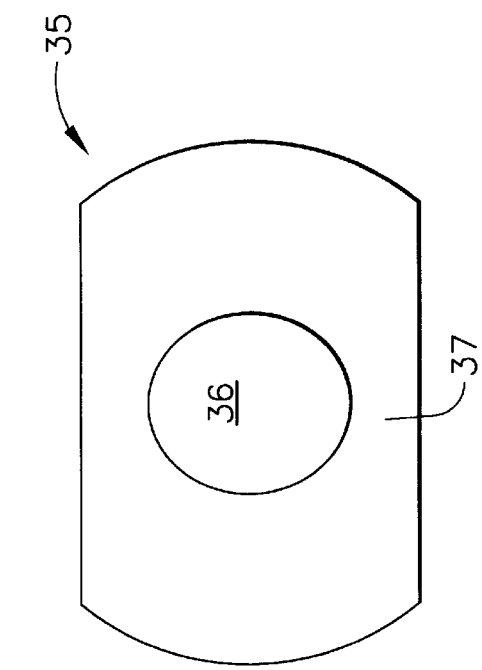
Figure 3E:
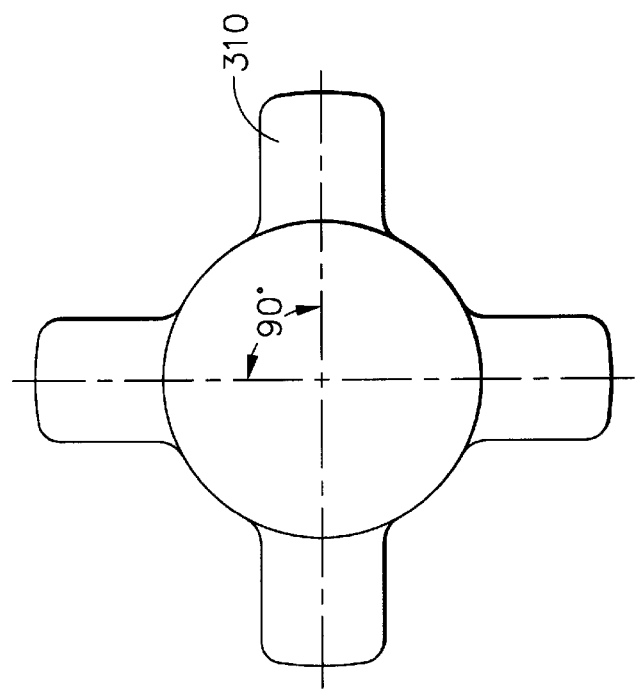
Figure 3C:
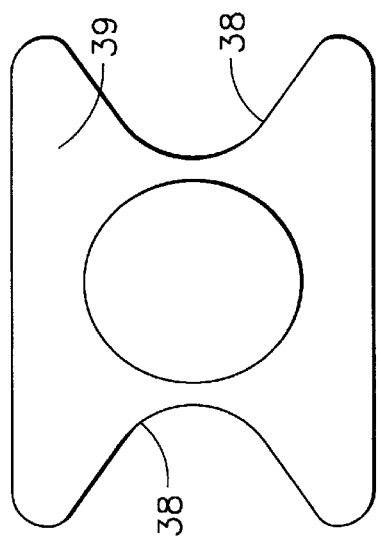
Figure 3D:
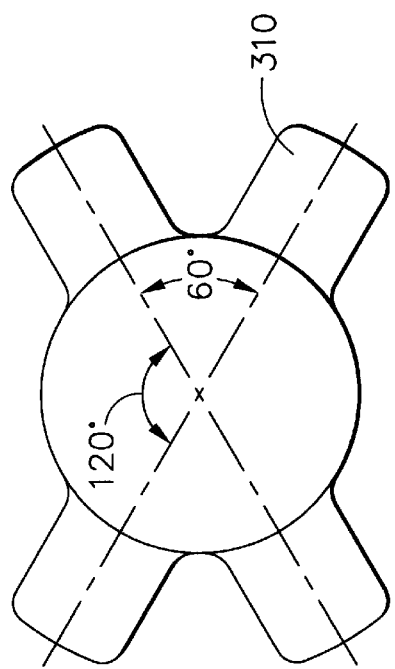

For a better understanding of the invention, the following description of the preferred embodiment should be taken in conjunction with the above-described drawings:

Particularly preferred embodiments of the present invention are shown in FIGS. 1b, 1c and 3b and may be made from one or more biocompatible, optically clear materials, for example silicone or the group of compounds known as acrylic polymers, such as polymethyl methacrylate (PMMA), polyhydroxymethyl methacrylate, or copolymers of silicone and methylmethacrylate, collagen/acrylic blends, or other known materials. Optical body (18) has an anterior surface (120) in a spherical shape to provide the prescribed optical correction. The posterior surface of the preferred embodiment has a slightly smaller radius (127) than the curvature of the haptic bodies (126) to assure there is no contact with the natural lens at its apex (148) during accommodation of the eye where the natural lens radius is reduced (see FIGS. 1c and 1g).

Figure 4A:
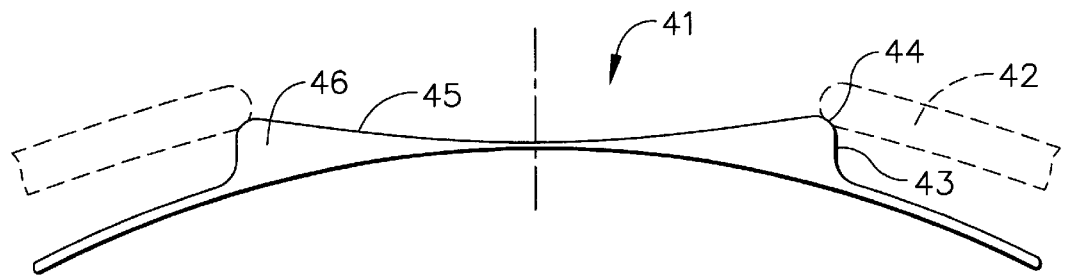
FIG. 4a shows a cross-sectional view of the lens (41) in relationship to the iris of the eye (42) as it touches the protruding annular surface (43) and, more particularly, the radiused corner (44) between the protruding annular surface (43) and the anterior surface (45) of the optical body (46).
Figure 4B:
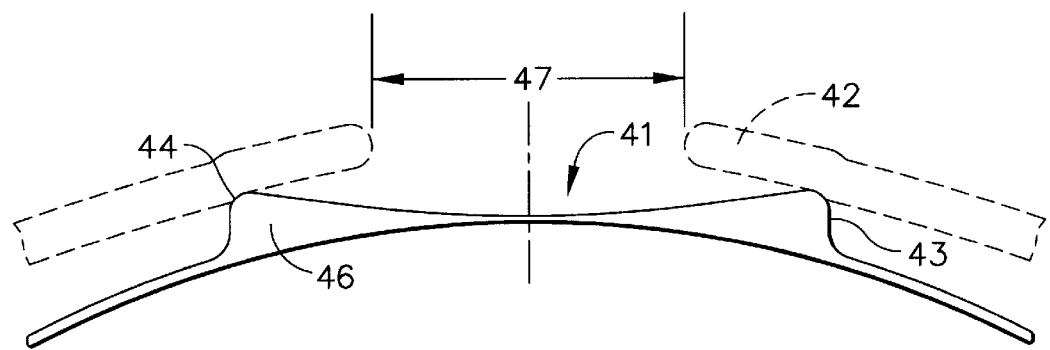
FIG. 4b shows a cross-sectional view of the lens (41) in relationship to the iris of the eye (42) after it has constricted to its constricted diameter (47), sliding over the protruding annular surfaces (43) allowing the iris (42) to ride over the optical body (46) while maintaining contact with the protruding annular surfaces (43) and, more particularly, the radiused corners (44) of the lens.
Figure 4C:
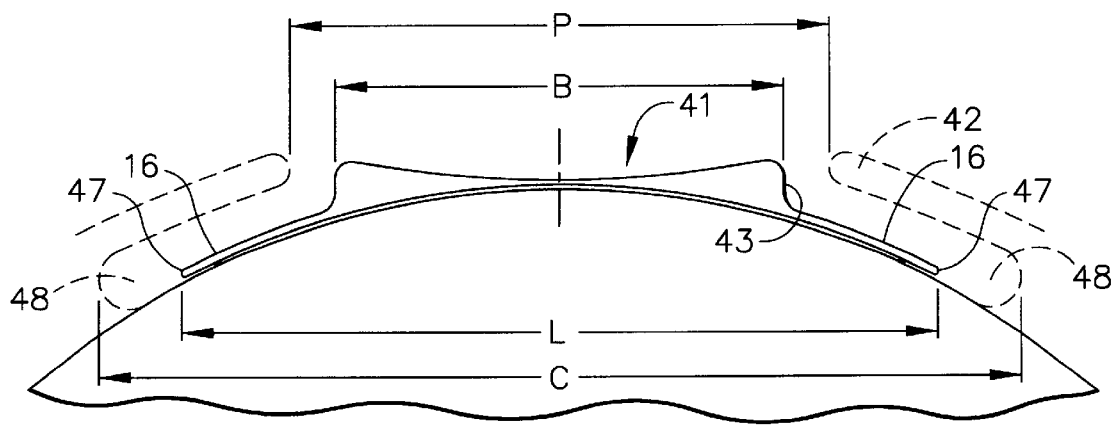
FIG. 4c shows a cross-sectional view of the lens (41) in relationship to the iris of the eye (42) and the area of the ciliary sulcus (48). When the iris (42) is fully dilated, the lens (41) is allowed to move. The range of motion of the lens (41) is determined by the relationship between the haptic diameter or diagonal dimension (L), the diameter of the eye at the ciliary sulcus (C), the fully dilated diameter of the patient's pupil (P), and the diameter of the annular protruding surface(s) (B).
Figure 5:
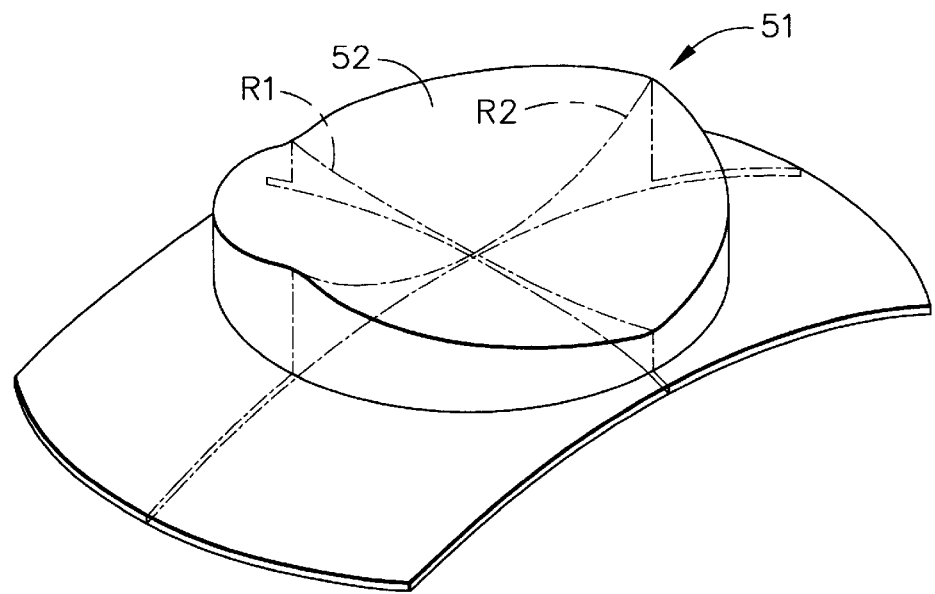
FIG. 5 shows an isometric view of an embodiment of the lens (51) where the anterior surface (52) of the lens (51) is toroidal shaped to correct astigmatism. Radius (R1) is larger than radius (R2) and a continuously smooth surface is generated between the radii (R1 and R2).
Figure 6:
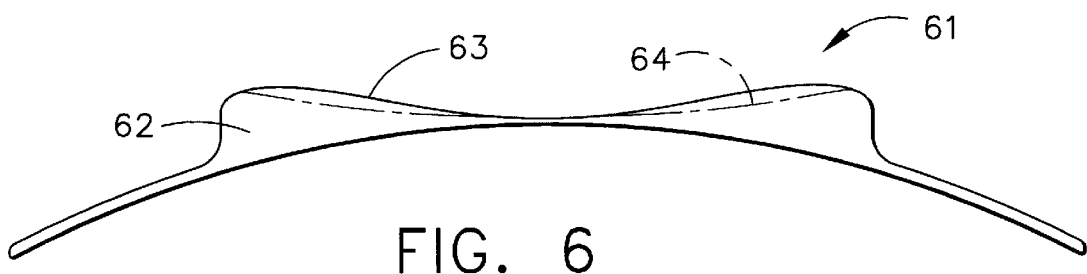
FIG. 6 shows a cross-sectional view of another embodiment of the lens (61) with an optical body (62) where the anterior surface (63) is aspherical to increase the visual acuity provided to the patient while maintaining the same optical power of the lens (61) as compared to a spherical surface (64) depicted by a dashed line.
Figure 7:
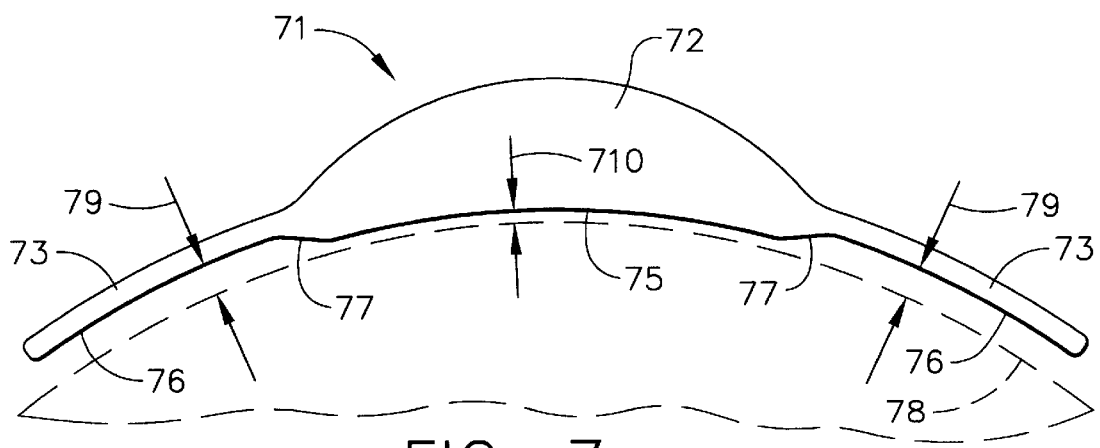
FIG. 7 shows a cross-sectional view of another embodiment of the present invention (71), the optical body (72) having a posterior concave surface (75) and haptic bodies (73) having a posterior concave surface (76) such that the two concave surfaces are stepped and connected by transitional surface(s) (77). Also shown is the curvature of the natural lens (78). Said step (77) between the posterior concave surfaces (75 & 76) creates a larger gap (79) at the haptic bodies (73) than the gap (710) at the optic body (72). This larger gap (79) permits increased fluid flow such that a greater amount of oxygen and nutrients reaches the natural lens.

Turning to FIG. 4c, annular protruding surface (43) protrudes into the pupil of the eye such that the iris of the eye (42) interferes slightly and provides a centering force to the lens. Once the lens is centered in the pupil of the eye, the iris rides up the annular protruding surface (43), which may be slightly ramped or curved at the edge (44) to assure no trauma to the iris (42), and slides over the optical body as shown in sequence in FIGS. 4a and 4b.

For lenses with very high corrective power (see FIGS. 2a, b and c), a smaller radius of curvature (23) is required and the optical body (22) may be stepped (21) to reduce the thickness of the lens such that it fits within the posterior chamber of the eye and does not substantially protrude into the anterior chamber. In FIG. 1a, a similar centering means exists with a positive lens (11) where an annular peripheral area (122) of the lens (11), that is sufficiently steep, protrudes into the path of the iris such that the iris will place a centering force on the lens as it constricts and slides up and over the convex anterior surface (14).

FIG. 1a shows a lens (11) with two haptic bodies (16) that are thin and substantially uniform in thickness (129) (thickness preferably no greater than about 0.15 mm) and are made from a flexible biocompatible material such that they can flex under very light loads in the direction of the optical axis (128). Now turning to FIG. 4c, the haptic bodies (16) have a diameter or diagonal measurement (L) from edge to edge (47) such that they are smaller than the diameter of the periphery of the posterior chamber (C) of the eye in the area of the ciliary sulcus (48). When diagonal measurement (L) is less than the width of the posterior chamber (C), the lens is allowed to float freely in the posterior chamber. However, the lens (41) is still held loosely in the eye such that the lens does not grossly decenter. The annular protruding surface(s) (43) must be held such that they are entirely within the pupil of the eye when dilated to its maximum aperture (P). Should the lens (41) decenter such that the protruding annular surface (43) is beyond the maximum aperture of the pupil (P), the protruding annular surfaces (43) will act to decenter the lens rather than to center it. Haptics (16) restrict this motion and keep the annular protruding surface (43) inside the dilated pupil (P). A similar action occurs with the positive lens (11) shown in FIG. 1a where the curvature of the lens itself protrudes (122) to receive a centering force applied by the iris as it constricts. Returning to FIG. 4c, the diameter of the outermost edges of the haptic(s) (L) is given by simultaneously meeting the following inequalities:

$$L \geq C - P + B$$

$$L \geq C/2 + P/2$$

$$L < C$$

where L is the largest diameter of a circle that the outermost edges of the haptic body(ies) will fit within;

C is the diameter of the eye at the ciliary sulcus;

P is the fully dilated diameter of the patients pupil; and

B is the diameter of the annular protruding surface(s).

Figure 2A:
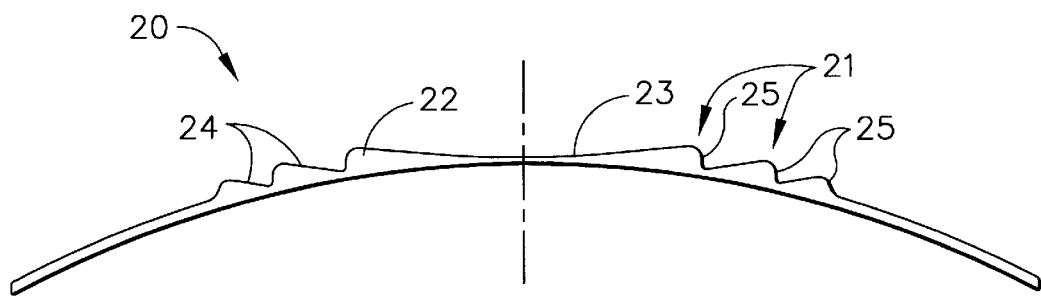
FIG. 2a shows a cross-sectional view of another embodiment of the present invention (20) where the optical body (22) has an anterior surface (23) which has two annular steps (21) to reduce the thickness of the lens. The steps (21) comprise annular, anterior surfaces (24) each of which is a continuation of the anterior surface (23) and annular protruding surfaces (25) to receive centering forces from the iris.
Figure 2B:
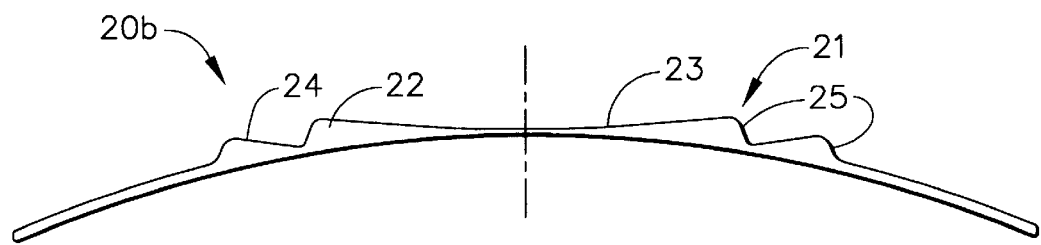
FIG. 2b is a cross-sectional view of another embodiment of the invention (20b) where there is only one step (21) in the optical body (22) creating one annular surface (24) which is a continuation of the anterior surface (23) of the optical body (22).

Should more than one annular protruding surface diameter (B) exist within a single embodiment (such as shown in FIG. 2a or 2b), each surface is calculated individually using its particular diameter (B) and any one or any combination of these surfaces must satisfy the above inequalities.

For a positive lens (11), shown in FIG. 1a, diameter B is measured at a point where the iris will contact the annular protruding surface with adequate force to center the lens; this is the diameter of the lens itself at an area (122) where the iris will contact it with adequate force to center the lens.

Figure 2C:
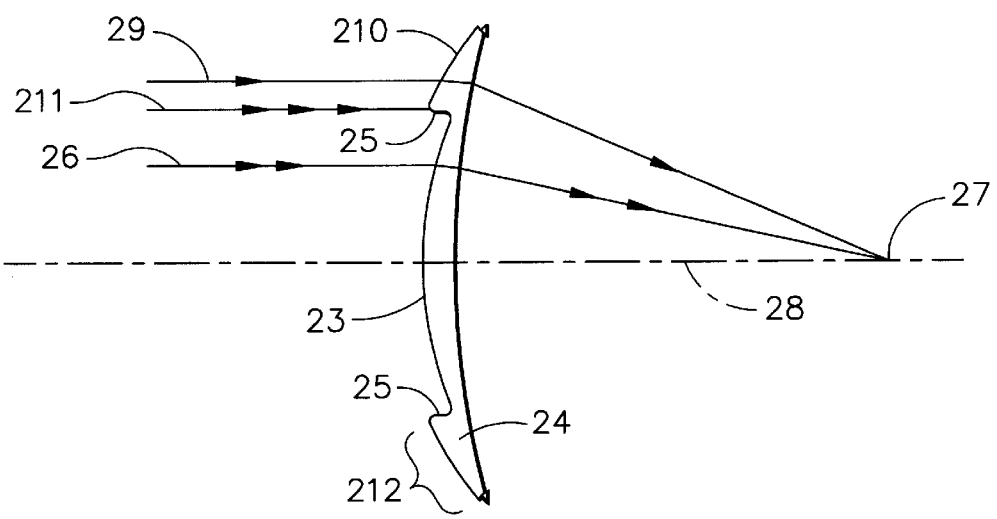
FIG. 2c is a cross-sectional view (with haptic bodies cut away) of the embodiment of the present invention where the concept of stepped surfaces is applied to a positive lens and shows the refractive characteristics of the lens. Ray (26) which is parallel to the optical axis of the lens (28) refracts through the inner annular lens surface (23) of the optical body (22) and intersects the optical axis (28) at the focal point (27). Ray (29) which is parallel to the optical axis (28) refracts through the outer annular surface (210) of the optical body (22) of the lens and also intersects the optical axis (28) at the same focal point (27). All rays refracted through both annular surfaces (23 and 210) will create a single image and these two surfaces will work as a single optical surface with reduced lens thickness. However, parallel ray (211) represents light passing through the radiused, chamfered, or sloped protruding surface (25) between the annular surfaces (23 and 210) which will not be refracted properly and will exit from the lens as scattered light. The optical body (24) has an annular peripheral area (212 and 210) that is sufficiently steep and protrudes into the path of the iris such that the iris will place a centering force on the lens as it constricts.

The intraocular corrective lens of the present application must include a protruding surface which allows the iris to slide over it without restricting the movement of the iris. It is this interaction between the protruding surface and the iris which keeps the lens centered in the eye. The protruding surface may be a part of the optical body itself, as in FIG. 1a, or it may be adjacent to but not a part of the optical body, as in FIG. 1b. It is also possible, although not preferred, that the protruding surface be wholly separate from the optic body. The protruding surfaces may be annular in shape and are generally sloped, curved or ramped at their edges in order to permit the iris to move comfortably over them. The protruding surfaces may also be stepped as shown in FIG. 2a, 2b or 2c. The height of the protruding surface is generally from about 0.25 to about 1.0 mm from the posterior surface of the lens. The optical body of the intraocular corrective lens, when placed in the eye, is located substantially in the posterior chamber of the eye behind the iris.

The structure of the optical body, which acts as the lens in the present invention, follows the requirements of standard optical theory. The lens may have a concave or convex surface (positive or negative optical power). It may be torroidal, spherical or aspherical in shape. The curvature of the lens will depend on the optical correction required for a particular patient, keeping in mind that the lens will be used together with the eye's natural lens. The precise structure of the optical body may, in part, determine the structure of the protruding surfaces required to center the lens. The lens is generally made from a flexible, biocompatible transparent material. Hydrophilic materials and gas permeable materials are preferred. Examples of such materials include, but are not limited to, silicones, silicone-methacrylate copolymers, polymethyl methacrylate, polyhydroxyethyl methacrylate, and collagen/acrylic blends. Mixtures or copolymers of those materials may also be used. The curvature of the optical body, and particularly the posterior surface of the optical body, relative to the curvature of the haptic bodies of the lens, as described above, is chosen to maximize the ability of the lens to float freely in the eye without interfering with the eye's natural lens and consistent with the optical characteristics required from the lens (optical body). The lens of the present invention, therefore, does not rest directly on the eye's natural lens.

One or more haptic bodies are included in the intraocular lens of the present invention. Examples of haptic structures which may be used are shown in FIG. 3. The haptics are made from the same types of materials that the optical body of the lens is made from. The haptics are generally substantially of uniform thickness and preferably have a thickness of no greater than about 0.15 mm. The haptics are generally not planar and, as discussed above, the radius of curvature of the haptics taken together with the radius of curvature of the optical body, helps determine the ability of the lens to float freely in the eye. It is preferred that the maximum diagonal haptic dimension of the lens (L) be from about 10.5 to about 11.5 mm. The haptic bodies should be flexible in the direction of the optical axis of the lens. The flexing of the haptic created by the natural dynamic action of the eye circulates or assists in circulating the aqueous fluid of the eye.

What is claimed is:

1. A phakic intraocular corrective lens having an anterior and a posterior side, comprising an optical body with is free of any openings between its anterior and posterior sides; a plurality of haptic bodies, said haptic bodies attached to and extending bilaterally from said optical body; an annular protruding surface of such size, shape and position that, when positioned in the eye, it will contact the iris at one or more points as the iris constricts to place a centering force on the lens, said protruding surface located on the anterior side of said lens; said lens configured such that when placed in the eye, the optical body is substantially in the posterior chamber of the eye behind the iris, and wherein the anterior side of the optical body is stepped forming up to three concentric rinds zones wherein the adjacent outer zones are displaced along the axis of the optical body relative to the adjacent inner zones to reduce the thickness of the optical body.

2. A method of fitting a phakic intraocular corrective lens in an eve of a wearer, said lens having an anterior and a posterior side and comprises an optical body which is free of any openings between its anterior and posterior sides, a plurality of haptic bodies attached to and extending bilaterally from said optical body: an annular protruding surface located on the anterior side of said lens; said method comprising selecting the shape and dimensions of said lens such that the haptic bodies are of such size that they cannot contact the outermost circumference of the ciliary sulcus of the wearer at the same time; said annular protruding surface being of such size, shape and position that, when positioned in the eye, it will contact the iris at one or more points as the iris constricts to place a centering force on the lens; and said lens configured such that when placed in the eye, the optical body is substantially in the posterior chamber of the eye behind the iris.

3. A method of fitting a phakic intraocular corrective lens in an eve of a wearer, said lens having an anterior and a posterior side and comprises an optical body; a plurality of haptic bodies attached to and extending bilaterally from said optical body; an annular protruding surface located on the anterior side of said lens; wherein the radius of curvature of the posterior surface of the optical body is substantially equal to the radius of curvature of the haptic bodies; said method comprising selecting the shape and dimensions of said lens such that the haptic bodies are of such size that they cannot contact the outermost circumference of the ciliary sulcus of the wearer at the same time said annular protruding surface being of such size, shape and position that, when positioned in the eye, it will contact the iris at one or more points as the iris constricts to place a centering force on the lens; and said lens configured such that when placed in the eye, the optical body is substantially in the posterior chamber of the eye behind the iris.

4. A method of fitting a phakic intraocular corrective lens in an eye of a wearer, said lens having an anterior and a posterior side and comprises an optical body having a negative curvature, a plurality of haptic bodies attached to and extending bilaterally from said optical body; an annular protruding surface located on the anterior side of said lens; wherein the protruding surface is adjacent to the optical body of the lens; said method comprising selecting the shape and dimensions of said lens such that the haptic bodies are of such size that they cannot contact the outermost circumference of the ciliary sulcus of the wearer at the same time; said annular protruding surface being of such size, shape and position that, when positioned in the eye, it will contact the iris at one or more points as the iris constricts to place a centering force on the lens; and said lens configured such that when placed in the eye, the optical body is substantially in the posterior chamber of the eye behind the iris.

5. The method according to claim 2 wherein the lens is selected such that the outermost diameter of the haptic bodies satisfies simultaneously the following formulas:

$$L \geq C-P+B$$

$$L \geq C/2+P/2$$

$$L < C$$

wherein L is the largest diameter of a circle that the outermost edges of the haptic bodies will fit within; C is the diameter of the eye at the ciliary sulcus; P is the fully dilated diameter of the patient's pupil; and B is the diameter of the protruding surface.

6. The method according to any of claims 2, 3 or 4 wherein, in the intraocular lens, the height of the protruding surface is from about 0.25 to about 1.0 mm from the posterior surface of the lens.

7. The method according to any of claims 2, 3 or 4 wherein, in the intraocular lens, the haptic bodies have a thickness no greater than about 0.15 mm.

8. The method according to any of claims 2, 3 or 4 wherein, in the intraocular lens, the maximum diagonal haptic body dimension is from about 10.5 mm to about 11.5 mm.

9. The method according to any of claims 2, 3 or 4 wherein the intraocular lens is made from a material selected from the group consisting of silicones, silicone-methacrylate copolymers, polymethyl methacrylate, polyhydroxyethyl methacrylate, collagen/acrylate blends, and mixtures and copolymers thereof.

10. The method according to claim 2 or 3 wherein the lens has a positive curvature and the protruding surface is a part of the optical body of the lens.

11. The method according to claim 2 or 3 wherein the lens has a negative curvature and a protruding surface adjacent to the optical body of the lens.

* * * * *

UNITED STATES PATENT AND TRADEMARK OFFICE
CERTIFICATE OF CORRECTION

PATENT NO. : 6,015,435
DATED : January 18, 2000
INVENTOR(S) : Igor Valunin
George W. Rozakis It is certified that error appears in the above-indentified patent and that said Letters Patent is hereby corrected as shown below:

Column 10, line 21, (claim 1) --rinds-- should read "rings"
Column 10, line 53, (claim 3) please insert ";" following the word "time"
Column 11, line 10, (claim 5) please delete --claim 2 -- and replace with words "any of claims 2, 3 or 4"

Signed and Sealed this

Twenty-fourth Day of October, 2000

Attest:

Q. TODD DICKINSON

*Attesting Officer*    *Director of Patents and Trademarks*